United States Patent
Pettit et al.

(10) Patent No.: US 6,723,527 B2
(45) Date of Patent: Apr. 20, 2004

(54) METHODS FOR DETERMINING TOXICITY REVERSING AGENTS

(75) Inventors: Flora H. Pettit, Austin, TX (US); William Shive, deceased, late of Austin, TX (US), by Gwyn White Shive, legal representative (73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 10/010,716

(22) Filed: Oct. 26, 2001

(65) Prior Publication Data

US 2003/0087331 A1 May 8, 2003

(51) Int. Cl.$^7$ ............................. C12Q 1/02; C12Q 1/00; G01N 33/53
(52) U.S. Cl. ........................ 435/29; 435/7.2; 435/7.24; 435/4; 424/900
(58) Field of Search .......................... 435/29, 7.2, 7.24, 435/4; 424/900

(56) References Cited

U.S. PATENT DOCUMENTS

| | | | |
|---|---|---|---|
| 4,499,064 A | 2/1985 | Shive | 424/2 |
| 6,297,014 B1 * | 10/2001 | Taylor et al. | 435/6 |

FOREIGN PATENT DOCUMENTS

WO       WO 99/60154       11/1999

OTHER PUBLICATIONS

Cox, S.; Antiviral Chem Chemother,; V. 2(1), p. 23–28; (1991).*

Bargossi et al., "Exogenous CoQ10 preserves plasma ubiquinone levels in patients treated with 3–hydroxy–3–methylglutaryl coenzyme A reductase inhibitors," *Int J Clin Lab Res.*, 24(3): 171–176, 1994.

Folkers et al., "Lovastatin decreases coenzyme Q levels in humans," *Proc Natl Acad Sci U S A*, 87(22):8931–8934, 1990.

Ghirlanda et al., "Evidence of plasma CoQ10–lowering effect by HMG–COA reductase inhibitors: a double–blind, placebo–controlled study," *J Clin Pharmacol*, 33(3):226–229, 1993.

Shive, "Development of lymphocyte culture methods for assessment of the Nutritional and metabolic status of individuals," *J. Int. Acad. Prev. Med.*, 8:5–16, 1984.

Shive et al., "Development of a chemically defined serum–and Protein–free medium for growth of human peripheral lymphocytes," *Proc Natl Acad Sci U.S.A.*, 83:9–13, 1986.

* cited by examiner

Primary Examiner—Louise N. Leary
(74) Attorney, Agent, or Firm—Fulbright & Jaworski L.L.P.

(57) ABSTRACT

Disclosed are methods for assessment of the ability of substances to ameliorate the toxic-effects of compounds based on a lymphocyte culture assay. The lymphocyte assay is a repeatable and quantitative assay for lymphocyte growth in a chemically defined media in which specific compounds with potential toxicity and substances with potential abilities to ameliorate the toxicity can be added to determine specific and individualized requirements for such substances. Also disclosed are methods for ameliorating side-effects by administering to a patient undergoing therapy with a drug that has a toxic-effect, a substance identified by the methods of the invention. Further provided is a composition that ameliorates the toxic-effect of the statin family of drugs. Methods and processes for partially purifying and/or isolating this composition are also provided. Thus, the methods of the invention not only provide substances for reversal of compound-toxicity but also provide methods for pre-approving compounds for human use.

41 Claims, 2 Drawing Sheets

METHODS FOR DETERMINING TOXICITY REVERSING AGENTS

BACKGROUND OF THE INVENTION

1. Field of the Invention

The present invention relates generally to the field of toxicology and more specifically to the toxicity or side effects to therapeutic and/or other compounds. More particularly, it concerns the development of methods for identifying and screening for substances that can ameliorate the toxic-effects of compounds, such as clinical drugs, food additives, and a variety of other chemical compounds, based upon assaying lymphocytes.

2. Description of Related Art

The impact of chemical intervention on the overall health of specific individuals is often uncertain. While a pharmaceutical may remedy the targeted defect, the treatment may be accompanied by serious side effects that can, in some cases be worse than the initial malady. In general, the side effects of a pharmaceutical preparation are known but may often be limited to a small subset of individuals. In such a subset, side effects may often be so severe that alternate therapies are required. In some cases, the severity of side effects in a small subset of those who would be taking a drug may prevent FDA approval.

In one example, a relatively new class of drugs called 'statins' function as metabolic inhibitors and are used widely to reduce cholesterol biosynthesis and hence, to reduce levels of cholesterol. The introduction of statins has led to a significant decrease in the mortality and costs associated with ailments involving cholesterol accumulation including atherosclerotic heart disease and stroke. However, a significant number of people who use statins experience side effects. Although the majority of these side effects are mild gasterointestinal ailments several cases of more severe neurological side effects have also been reported. In such cases statin therapy has to be terminated to relieve the side effects. Whether mild or severe side effects in general pose severe deterrents to any drug therapy, especially in the case of drugs that have long-term preventive benefits. Thus, there is an acute need in the art to identify and screen for substances that can counteract side effects of drugs such as statins that cause side effects.

The present inventors have previously developed a specific lymphocyte culture medium and a lymphocyte culture assay which facilitated the assessment of deficiencies or abnormal requirements of nutrients; sensitivity to nutrient imbalances; sensitivity and/or predisposition to side effects of drugs, and/or nutrients, and/or a wide variety of other compounds in an individual (see U.S. Pat. No. 4,499,064, incorporated herein by reference). Although, the inventors previous invention provides methods to predetermine which individuals will experience side effects to a particular compound there is no cost-effective in vitro method in the art to identify substances that can overcome side effects of drugs or other compounds.

SUMMARY OF THE INVENTION

The instant invention overcomes the defects in the art and provides a reliable, safe and effective means of identifying substances that can overcome, ameliorate or at least reduce side effects or toxic-effects or sensitivities to different compounds that an individual may experience.

Provided is a method for testing a substance for the ability of the substance to ameliorate the toxic-effects of a compound, comprising the steps of: a) incubating lymphocytes in the presence of the compound and in the presence and absence of the substance; and b) comparing the toxic-effect of the compound on the lymphocytes incubated in the presence of the substance to the effect of the compound on the lymphocytes in the absence of the substance.

In some aspects the method further comprises incubating the lymphocytes in a chemically-defined media. Growing human lymphocytes or any other cell in a chemically-defined medium allows examination of the effects of addition or removal of different components to the medium on cell growth. Chemically-defined media, specifically designed for the growth of human lymphocytes, is described by the present inventors in U.S. Pat. No. 4,499,064, the entire text of which is incorporated herein by reference.

In some embodiments, it is contemplated that the method will further comprise a control comprising: a) incubating the lymphocytes with a compound with a known toxicity in the presence of a substance known to reverse the known toxicity; and b) analyzing the effect on lymphocytes.

In other embodiments, the method further comprises testing a range of concentrations of a substance identified by the method of the invention to obtain the lowest possible dosage at which the substance can reverse the toxic effect of the compound.

In one embodiment, the toxic-effect of the compound is assessed by assessing its effect on the growth of the lymphocytes. In one such embodiment, the growth rate of the lymphocytes is measured. Methods for measuring the growth rate and/or proliferation of lymphocytes are well known in the art. For example, the most widely used method for measurement of cell growth or cell proliferation is assaying the incorporation of tritiated thymidine ($^3$H-thymidine) in cells which is proportional to the rate of DNA synthesis. Other examples include a range of colorimetric procedures such as the MTT assay, the XTT assay, the MTS assay, etc., most of which are based on tetrazolium salts which produce highly colored dyes in response to the metabolic activity of viable cells. The present inventors also intend to use assays that measure the amount and synthesis of ATP in cells using bioluminescence based assays.

In other embodiments, the toxic-effect of the compound is assessed by assessing the effect of such a compound on other responses of lymphocytes. In one such embodiment, the effect of a toxic compound on the cell size of lymphocytes may be measured. In yet another embodiment, a change in the morphology of lymphocytes in response to a toxic compound may be measured. Such measurements may comprise visual identification using microscopic methods. Alternatively, the measurement of a biochemical parameter such as an enzyme activity may be used to access the toxic-effect of the compound on a lymphocyte.

Various types of compounds are known that cause side effects or toxicity. Such compounds include but are not limited to, clinical drugs, teratogenic agents, social drugs, drug additives and stabilizers, food additives, food coloring agents, food components, herbs, herbal extracts, and any other chemical compound that can cause toxicity. The compounds also include agents that are accidentally consumed, for example, certain non-edible mushrooms, non-edible plants, etc.

In one embodiment of the method, the clinical drug is a metabolic inhibitor. In one such aspect the metabolic inhibitor is a statin. The statins are a group of drugs widely used to reduce cholesterol biosynthesis and have proven to be very effective in reducing mortality due to conditions that are caused by cholesterol accumulation in veins such as myocardial infarctions and strokes. Statins are inhibitors of HMG CoA reductase, a liver enzyme involved in cholesterol synthesis. Statins provide a long-term preventive effect on the accumulation of cholesterol. However, a significant percentage of the population suffers from side effects of statins which include a host of mild to severe gasterointestinal effects, muscular inflammation, and peripheral neuropathies. These side effects are remedied by stopping the statin therapy. Given the beneficial effects of statins, termination of statin therapy hinders the long-term health goals sought. The methods of the present invention provide substances that can counteract statin side effects, thereby allowing the continuation of the statin therapy in individuals. In specific aspects, the methods of the invention may be used to identify substances that reverse the toxicity of a statin such as lipitor (Atorvastatin), mevacor (Lovastatin), pravachol (Pravastatin sodium), zocor (Simvastatin), Baychol, Cerivastatin, Fluvastatin and the like.

In another embodiment of the method, the clinical drug is a sedative. Non-limiting examples of sedatives include, but are not limited to, benzodiazepines such as diazepam.

In yet another embodiment, the clinical drug is a chemotherapeutic agent used for cancer therapy and is exemplified by methotrexate, doxorubicin, daunorubicin, mitomycin, actinomycin D, bleomycin, plicomycin, taxol, vincristine, vinblastine, cisplatin, VP16, carmustine, melphalan, cyclophosphamide, chlorambucil, busulfan, lomustine, carboplatin, procarbazine, mechlorethamine, camptothecin, ifosfamide, nitrosurea, tamoxifen, raloxifene, estrogen receptor binding agents, gemcitabien, navelbine, farnesyl-protein transferase inhibitors, transplatinum, 5-fluorouracil, or temazolomide.

In still other embodiments of the method, the clinical drug is an anti-inflammatory agent. In specific embodiments, the anti-inflammatory agent may comprise salicylate, and/or acetyl salicylate and may include ibuprofen, ketoprofen, piroxicam, naproxen, naproxen sodium, sulindac, aspirin, choline subsalicylate, diflunisal, oxaprozin, diclofenac sodium delayed release, diclofenac potassium immediate release, etodolac, ketorolac, fenoprofen, flurbiprofen, indomethacin, fenamates, meclofenamate, mefenamic acid, nabumetone, oxicam, piroxicam, salsalate, tolmetin, magnesium salicylate. In other specific embodiments, the anti-inflammatory agent may be a steroid-based agent such as a corticosteroids and is exemplified in non-limiting examples by dexamethason, hydrocortisone, methylprednisolone, prednisone, triamcinolone, etc.

In yet other embodiments of the method, the clinical drug can be isoniazid, valproic acid or retinol.

In one aspect of the invention, the compound can be a teratogenic agent such as thalidomide.

In other aspects of the invention, the compound is a chemical compound such as a food additive, a food component, a color additive, a drug additive and/or a drug stabilizer. Non-limiting examples of food additives include monosodium glutamate, aspartame or saccharin. Non-limiting examples of drug additives include aluminum salts, dyes to color drugs, flavoring agents.

In other embodiments, the compound that causes side effects can be a component of a social drug. For example, various social drugs such as alcoholic beverages comprise ethanol; other social drugs such as coffee, chocolates and some carbonated beverages comprise caffeine; yet other social drugs such as tea's comprise theophylline, theobromine and caffeine. Side effects caused by such compounds are well known. For example, caffeine, which is a component of coffee, chocolate, colas, and several across the counter drugs, is a central nervous system (CNS) stimulant. At a dosage of 50–100 mg, which is the typical amount in one cup of coffee, an apparent temporary increase in mental clarity and energy levels, with a reduction in drowsiness is seen. At higher doses caffeine causes hyperstimulation. Caffeine also stimulates the cardiovascular system, raising blood pressure and heart rate. Other side effects of caffeine include its diuretic and mild laxative properties. Caffeine and other methylxanthines such as theophylline and theobromine, also increase the respiratory rate and act as bronchodialators. Yet other side effects of higher doses of caffeine intake by pregnant women include birth defects.

The methods of the invention are useful to test substances for their ability to ameliorate toxic-effects and/or side effects of various compounds such as those listed above. However, it will be recognized by the skilled artisan that the invention is in no way limited to the compounds described above and that the methods of the present invention may be used to identify substances that can ameliorate the toxic-effects of virtually any type of chemical or biological compound.

The invention further provides methods that can screen for and identify substances with abilities to reduce toxic-effects. It is contemplated that the substances identified by the method will comprise a wide range of substances such as naturally-occurring substances, and man-made or synthetic substances. These include nutritional supplements, amino acids, proteins, peptides, nucleic acids, oligonucleotides, polynucleotides, lipids, vitamins, drugs, other chemical substances, and other biochemical substances such as those isolated from plants, animals, etc.

The invention also provides a method for ameliorating toxicity in a patient undergoing therapy with a compound that has a known toxicity or side-effect comprising, administrating to the patient a substance identified in accordance with the method of the invention as described above.

It is envisioned that the method of the invention will be useful in the context of human patients. The methods of the present invention may be applicable to other mammalian patients as well. In such embodiments, the media used to culture lymphocytes will be tailor-made to the specific mammal. As will be appreciated by one of skill in the art the nutrient requirements of lymphocytes of different species will vary. Some other mammals contemplated include horses, dogs, cats, cows, sheep.

Also provided by the present invention are methods for ameliorating toxicity in a patient undergoing therapy with a compound that has a known toxicity or side-effect comprising; a) isolating lymphocytes from the patient; b) incubating lymphocytes in the presence of the compound and in the presence and absence of a candidate substance that can reverse the toxicity of the compound; c) comparing the toxic-effect of the compound on the lymphocytes incubated in the presence of the candidate substance to the effect of the compound on the lymphocytes in the absence of the candidate substance thereby identifying a substance that can reverse toxicity; and d) administrating to the patient the identified substance that can reverse toxicity of the compound.

The invention also provides a composition that has the ability to ameliorate the toxic-effects of a metabolic inhibitor. Thus, provided is a composition comprising one or more factors characterized by the following properties: a) isolatable from mammalian plasma; b) containing at least one heat-labile component having a molecular weight of at least 100,000; and c) having the ability to ameliorate the toxicity of a metabolic inhibitor.

In specific aspects, the composition of the invention has the ability to ameliorate the toxic-effects of metabolic inhibitors such as, the statins which are exemplified by, lipitor (Atorvastatin), mevacor (Lovastatin), pravachol (Pravastatin sodium), zocor (Simvastatin), Baychol, Cerivastatin, or Fluvastatin. By 'ameliorating the toxic-effects' it is meant that the composition can decrease, reduce, eliminate, or reverse the side effects caused by the statins.

The present inventors have also found that the composition comprised of one or more plasma factors is either lacking or deficient in the plasma of certain individuals. The lymphocytes of these individuals show toxic responses to statins. Furthermore, transfer of plasma from an individual whose lymphocytes do not exhibit toxic responses to statins to an individual who lacks or is deficient in the composition reverses or ameliorates the toxic effect.

Thus, in one embodiment, the mammalian plasma from which the composition is can be isolated is human plasma. It is contemplated that one may also use plasma from other mammals such as monkeys, horses, cows, pigs, sheep etc, to isolate the composition.

Additionally, the present invention also contemplates identifying the plasma factors of the composition by testing the efficacy of some known proteins and factors and testing their efficacy at ameliorating statin toxicity. In one such embodiment, the present inventors contemplate testing the LDL-particle for its ability to ameliorate the toxicity of statins. LDL-particles comprise apoB-100 and cholesteryl esters and circulate in the blood stream. LDL receptors on cells recognize these LDL-particles and take up the LDL-particle by endocytosis. The endosome containing the LDL-particle is then translocated to the lysosome where enzymes hydrolyze the cholesteryl esters, releasing cholesterol and fatty acids into the cytosol. The apoB-100 protein is also degraded into amino-acids in the lysosome. As the LDL-particles are involved in the uptake of cholesterol into cells, the present inventors contemplate that they may have a role in the regulation of statin toxicity. As described above and elsewhere in the specification, statins are inhibitors of HMG-CoA reductase, an enzyme involved in the synthesis of cholesterol.

As used herein the specification, "a" or "an" mean one or more. As used herein in the claim(s), when used in conjunction with the word "comprising", the words "a" or "an" mean one or more than one. As used herein "another" mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

DESCRIPTION OF ILLUSTRATIVE EMBODIMENTS

The present inventors have previously demonstrated that the toxicity or potential for toxicity of different compounds can be determined by comparing the growth of lymphocytes in the presence and absence of a given compound. The growth of lymphocytes is monitored in a lymphocyte-growth specific medium developed by the present inventors in the presence or absence of the compound to be tested (U.S. Pat. No. 4,499,064, incorporated herein by reference). Growing human lymphocytes in a chemically-defined protein-free medium allows examination of the effects of addition or removal of different components to the medium on cell growth.

The present invention provides effective screening and testing methods to identify substances that can reduce or ameliorate the toxicity of compounds. Accordingly, by the methods of the present invention, the toxicity of a compound can be determined by measuring the inhibition of lymphocyte growth following the addition of the compound to the growth medium that lymphocytes are incubated in. One can then identify a substance that can ameliorate toxicity, by incubating the lymphocytes in the presence of a candidate substance that has a potential to ameliorate the toxic-effect in the continued presence of the compound that induces toxicity, and comparing lymphocyte growth. An increase in lymphocyte growth or a reversal of any other lymphocyte response as described above, in the presence of such a candidate substance allows the identification of a substance that is effective in ameliorating toxicity. Thus, several candidate substances, with the potential to ameliorate toxicity to various drugs and other compounds may be screened by the methods of the present invention.

Methods for measuring the growth rate of lymphocytes are well known in the art. For example, cell growth can be monitored by assaying the incorporation of tritiated thymidine ($^3$H-thymidine) into lymphocytes which is proportional to the rate of DNA synthesis of the lymphocyte. Other examples include calorimetric assays that measure the metabolic activity of viable cells using tetrazolium dyes and are exemplified by the MTT assay, the XTT assay, the MTS assay, etc. Yet other examples include bioluminescence-based assays that measure ATP synthesis in cells.

The present inventors also contemplate that the toxic-effect of a compound can be assessed by analyzing the effect of such a compound on other responses of lymphocytes. These 'other responses' include changes in cell size, changes in cell morphology, or changes in enzyme activity of specific enzymes in response to a toxic compound. Such responses may be detected by visual identification using microscopic methods or biochemical methods to measure changes in enzyme activity.

In one embodiment, the instant invention, focuses on identifying substances that can reduce/ameliorate/prevent the inhibition of lymphocyte growth by chemicals that act as metabolic inhibitors, such as, the statin family of drugs. The statin family of drugs include cholesterol biosynthesis inhibitors such as, Atorvastatin (lipitor), Baychol, Cerivastatin, Fluvastatin, Lovastatin (mevacor), Pravastatin sodium (pravachol) or Simvastatin (zocor), which are currently prescribed to a large population of patients for preventive and therapeutic purposes. Commonly experienced side-effect in patients on therapy with a statin include constipation, flatulence, indigestion, and abdominal pain. More serious side effects of the statins that lead to discontinuation of therapy include inflammation of muscles and neuropathies such as numbness and/or weakness and/or loss of sensation and/or abnormal sensations, dizziness, headache, insomnia, tingling, memory loss, anxiety, depression, tremor, loss of balance, and/or psychic disturbances.

By employing the methods of the present invention one can initially predict the potential for the development of toxicity and the extent of the toxicity in an individual by culturing lymphocytes isolated from an individual in the presence of a statin. More importantly, one can then screen for substances that have the ability to inhibit the side effects of the statins in that individual (or in a population) and thereby identify substances that can ameliorate toxicity. Thus, the methods of the present invention provide a means for reducing the toxic-effects of a drug by prescribing to a patient a combination of the substance and the statin (or other drug) such that the patient is benefited from the beneficial cholesterol lowering ability of the statin (or beneficial effect of the other drug) and at the same time not affected by the side effects of the drug. The inventors envision that the methods of the present invention are applicable to a wide variety of compounds in addition to clinical drugs.

The invention thus provides an effective therapeutic regimen for an individual patient by first, testing the effect of a drug on the individual patient's lymphocytes to determine if the drug causes a toxicity in that patient before the medication is prescribed. If a toxic-effect is seen, the patient is prescribed a therapeutic regimen that comprises a substance that can ameliorate the toxic-effect in conjunction with the drug.

The inventors envision that the methods of this invention will be used to evaluate all compounds as a part of pre-approving compounds for human use. Additionally, the inventors envision that the methods of the present invention will also be used to evaluate compounds before they are prescribed to individuals, as individual toxicities can vary over that of a population. Suitable substances may then be identified that prevent or reduce or ameliorate the toxicity caused by the compounds in the general population and/or in an individual as required. Therefore, this method provides a valuable first step in approving the use of a particular compound for human use, including uses for human clinical trials, use in food products, and in assessing the toxicity of various compounds encountered by the general public in common drug-additives, over the counter medications, herbs, and herbal extracts, house-hold chemicals, etc.

Another embodiment of the invention provides a composition comprised of one or more factor(s) present in the plasma which has the ability to ameliorate the toxic effect of the statin family of metabolic inhibitors. The inventors have shown herein that patients who have this composition or factor(s) in their plasma do not experience the toxic effects of the statins and this is reflected by the lymphocyte assay which shows no toxicity when lymphocytes are incubated with a statin in the presence of the patients plasma. In other patients, the plasma factor(s) in conjunction with supplemented co-enzyme Q (CoQ), ameliorates the toxicity. However, in some patients, the plasma with or without CoQ does not ameliorate the statin toxicity. Furthermore, the inventors have also shown that transfer of plasma from an individual that has no statin toxicity, and hence has the plasma composition or plasma factor(s), to an individual who is deficient or lacking the plasma composition, ameliorates the statin toxicity. Therefore, the inventors contemplate that either partially purifying or isolating the plasma factor(s) and administering the factor(s) in conjunction with a statin therapy will ameliorate the toxicity in patients that lack this endogenous composition or plasma factor(s).

Additionally, the inventors also contemplate identifying the plasma factor(s) or plasma composition by testing the efficacy of some known proteins and factors and testing their efficacy at ameliorating statin toxicity. In one such embodiment, the present inventors contemplate testing the LDL-particle for its ability to ameliorate the toxicity of statins.

A. Lymphocyte-Specific Media and Lymphocyte Assay

Several years ago, the present inventors developed a method for the assessment of the nutritional variability of cell cultures derived from individuals. The method involved the culture of lymphocytes in a chemically defined medium without the usual supplementation of fetal calf serum. Although activation of lymphocytes under serum-free conditions had been reported, growth of lymphocytes under serum-free conditions had never been reported. As difficulties were reported in achieving the same results in different laboratories it was suggested that possibly trace serum contaminants or other artifacts were involved in the serum-free experiments. Serum albumin or unidentified serum macromolecules were reported to be absolutely essential for mitogen-induced DNA synthesis in human peripheral blood lymphocytes. It became apparent that new media would have to be developed in order to obtain significant growth responses in a chemically defined media. In order to obtain media suitable for assessment of the nutritional status of lymphocytes, it was necessary to develop a medium in which components were adjusted to minimal concentrations but at a level which would still not limit the optimal response of the lymphocytes. Each change required determination of the effect on the response of other components. The present inventors developed such a medium that is chemically-defined and specific for the growth of human lymphocytes (see U.S. Pat. No. 4,499,064, the entire text of which is incorporated herein by reference).

Use of this media facilitated the assessment in an individual for deficiencies or abnormal requirements of nutrients, sensitivity to nutrient imbalances, sensitivity to toxic-effects of drugs, nutrients, and a wide variety of other compounds. This medium also facilitated the determination of the nutritional status and nutrient requirements of an individual so that effective utilization of nutrition by the individual could be determined and implemented. The media was however not applied to determining means of overcoming particular drug side-effect.

a. Culture Media

Exemplary culture medium for use in the context of the instant invention, also described in U.S. Pat. No. 4,499,064, incorporated herein by reference, comprises a serum-free, buffered solution of inorganic salts, glucose, amino acids, vitamins, pyruvate, choline, inositol and adenine. The pH is adjusted to 7.6. An antibiotic supplement is added to assist in suppression of contamination by other organisms, and calcium chloride and magnesium sulfate solutions, ferrous sulfate and ethylene-diamine tetraacetic acid (EDTA) are included. Deionized water is included to provide a final volume and the culture medium is filtered through filter units for sterilization. After filtration, a mitogen such as a sterile solution of phytohemogglutinin (PHA) is added to the culture medium. A more detailed description of the concentrations and ingredients of the culture medium is presented below:

(i) Solutions

Double Strength Medium Buffer. The double strength medium buffer used contains per liter of deionized water: Hepes (buffer), 23.8 g; sodium hydroxide, 1.28 g; sodium chloride, 14.02 g; dipotassium hydrogen phosphate, 1.05 g; and phenol red, 2.48 mg. This buffer is filtered through a 0.22 μm Millipore filter.

Medium Salts. The medium salts stock solution used for washing and suspending the lymphocytes is prepared by diluting the double strength medium buffer 1:2 with deionized water. Glucose when used as an optional component is added to a final concentration of 4 mM. The pH is then adjusted to 7.6 with 4N NaOH and the solution is filtered. Supplements are added to a measured amount of this stock solution giving a final concentration of 55.5 mg/l calcium chloride, 60.0 mg/l magnesium sulfate, 0.695 mg/l ferrous sulfate and 0.373 mg/l EDTA. The ferrous sulfate and EDTA are prepared and added together. The final solution is then refiltered. In tests for mineral requirements, the appropriate minerals are omitted from the medium salts.

Amino Acid Supplement. The amino acid supplement used at a lower limit contains per liter: 0.7 g L-arginine, 5.85 g L-glutamine, 0.25 g glycine, 0.23 g L-histidine, 0.13 g L-isoleucine, 0.44 g L-leucine, 1.22 g L-lysine, 0.15 g L-methionine, 0.0825 g L-phenylalanine, 0.35 g L-serine, 0.4 g L-threonine, 0.034 g L-tryptophan, 0.063 g L-tyrosine, and 0.39 L-valine. Generally, a 5×concentration for all amino acids except glutamine and cysteine are used for optimal results. If desired the glutamine can be added separately. Cysteine is added separately with pyruvate, as subsequently indicated.

Vitamin Supplement. The vitamin supplement used contains per liter: 0.735 mg biotin, 0.602 mg folinic acid (calcium salt), 0.61 g nicotinamide, 23.8 mg calcium pantothenate, 6.15 mg pyridoxine, 33.7 mg thiamin, 13.6 mg vitamin $B_{12}$, and 3.75 mg riboflavin.

Antibiotic Supplement. The antibiotic supplement used contains per liter: 10,000,000 IU penicillin, 10,000,000 μg streptomycin and 25,000 μg amphotericin B (Fungizone).

Phosphate Buffered Saline. The phosphate-buffered saline solution contains per liter: 7.1 g NaCl, 2.17 g $Na_2HOP_4 \cdot 7H_2O$, 200 mg $KH_2PO_4$ and 200 mg KCl.

(ii) Culture Medium

Culture medium suitable for the growth of human lymphocytes is prepared as follows: To 50 ml of medium buffer 72 mg glucose is added, 1 ml amino acid supplement, 1 ml of a 16.5 mg/ml pyruvate: 2.64 mg/ml cysteine solution, 1 ml of a 1.4 mg/ml choline chloride; 1.8 mg/ml inositol solution, 1 ml of the above indicated vitamin supplement, and 1 ml of a 135 μg/ml adenine solution. The pH is adjusted with dilute NaOH to 7.6. Supplements of the following are then added: 1 ml of the antibiotic supplement, 0.5 ml of a 22.2 mg/ml calcium chloride solution, 0.5 ml of a 24 mg/ml magnesium sulfate solution, 1 ml of a solution of 0.278 mg/ml ferrous sulfate in 0.149 mg/ml EDTA. Deionized water is added to a final volume of 100 ml and the medium is filtered through Nalgene membrane filter units for sterilization. After filtration 0.2 ml of a 1 mg/ml sterile solution of phytohemagglutinin (PHA) is added to each 100 ml of media. PHA is obtained from Sigma Chemical Co. in 5 mg quantities and is diluted with sterile, deionized water.

Accordingly, a culture medium suitable for determining the growth or other responses of lymphocytes comprises a serum-free, buffered (pH 7.6) solution in deionized water comprises per liter of solution the following components as described in Table 1:

TABLE 1

| Component | Concentration per liter |
|---|---|
| Carbohydrates | |
| Glucose | 720 mg. |
| Amino Acids: | |
| l-Arginine hydrochloride | 7 mg. |
| l-Cysteine hydrochloride hydrate | 26.4 mg. |
| l-Glutamine | 58.5 mg. |
| Glycine | 2.5 mg. |
| l-Histidine hydrochloride hydrate | 2.3 mg. |
| l-Isoleucine | 1.3 mg. |
| l-Leucine | 4.4 mg |
| l-Lysine hydrochloride | 12.2 mg |
| l-Methionine | 1.5 mg |
| l-Phenylalanine | 0.825 mg |
| l-Serine | 3.5 mg |
| l-Threonine | 4.0 mg |
| l-Tryptophan | 0.34 mg |
| l-Tyrosine | 0.63 mg |
| l-Valine | 3.9 mg |
| Vitamins: | |
| Biotin | 7.35 μg |
| Folinic acid (calcium salt) | 0.602 μg |
| Nicotinamide | 0.61 mg |
| Pantothenic acid (hemicalcium salt) | 238 μg |
| Pyridoxine hydrochloride | 61.5 μg |
| Thiamin chloride hydrochloride | 337 μg |
| Vitamin $B_{12}$ (Hydroxocobalamin hydrochloride) | 136 μg |
| Riboflavin | 0.375 μg |
| Salts (Inorganic): | |
| Calcium chloride | 111 mg |
| Magnesium sulfate/$7H_2O$ | 246.5 mg |
| Dipotassium hydrogen phosphate | 525 mg |
| Sodium hydroxide | 640 mg |
| Sodium chloride | 7.01 g |
| Ferrous sulfate heptahydrate | 2.78 mg with 1.49 mg EDTA (Ethylene diamine tetraacetic acid, disodium salt) |
| Other Components: | |
| Inositol | 18 mg |
| Hepes Buffer | 11.9 g |
| Choline chloride | 14 mg |
| Phenol red | 1.24 mg |
| Sodium pyruvat | 165 mg |
| Adenine | 1.35 mg |
| Antibiotic solution: | |
| Penicillin, | 100,000 IU |
| Streptomycin | 100,000 μg |
| Amphotericin B (Fungizone) | 250 μg |
| Mitogen: | |
| Phytohemagglutinin (PHA) | 2.0 mg |

In the culture medium of Table 1, glucose can be replaced by a substance which can produce glucose as a metabolic product, ferrous sulfate can be replaced by transferrin, ferric ions cannot be used effectively by themselves, except with transferrin, serine can be omitted under certain conditions in making certain tests, and in well nourished individuals only pantothenic acid stores allows very low growth of lymphocytes, but cellular deficiencies of niacin are rare in a population consuming fortified foods but can be detected in some individuals.

The components of the culture medium of Table 1 can be varied. In general, effective amounts of the components are used and can vary widely for the various growth assays of the invention and for individual patients. An effective amount of a component, as used herein, is an amount which will obtain a desired response from the patient. Preferably, the amount of the component should not fall significantly below the maximum for the dose response curve of the particular component for the patient when testing for other components. For most patients and assays the following ranges of components are satisfactory. The precise amounts of the components to provide an effective response can be determined by simple experimentation with the culture medium.

Glucose. In Table 1 is indicated the preferred media level of glucose for routine testing, i.e., 720 mg/l. Routine testing can be done with glucose concentration as high as 7200 mg or 7.2 g/l and as low as 72 mg/l. However, for carbohydrate replacement tests the levels from approximately 8 to 72 mg/l are the most useful for determining the ability of cells to utilize glucose relative to other carbohydrates or to test for substances which spare the amount of glucose needed.

Amino acids. The preferred levels of amino acids are 5×those listed in Table 1 for routine testing; however, if all of the amino acids are increased in the same amount relative to the concentrations indicated in Table 1, useful data can be obtained with no significant decrease in response with a 20 fold increase in the concentrations. At 40 fold, inhibition begins to become apparent and at 60–80 fold, inhibition of response by amino acids can preclude useful routine tests. The amount of the amino acids can collectively be decreased slightly and individually can be decreased below the concentration of that indicated by Table 1 from 0.3 to 0.1 of that level and still provide useful information. For determination of amino acid requirements, the dose response for half-maximal response would usually be in the approximate range of 0.1 times the amount listed in Table 1 with some in the range of 0.03 times the amount listed in Table 1. For test of imbalance, the amino acids have been added at high levels, for example 6–10 times higher than normal blood levels with useful results.

Pantothenic acid. Responses can be obtained with as little as about one-twentieth the amount listed in Table 1, and the upper limit is open for it is non-toxic even at very high relative levels. Dose-responses which are important are obtained by varying the levels and begin at about 10 $\mu$g/l of medium. Optimal response occurs well below the level listed in Table 1 and the toxicity level is very high.

Riboflavin. The response of lymphocytes to riboflavin begins to occur significantly at a concentration of 0.001 times that indicated in Table 1 and maximal response, which varies for different deficient individuals, occurs between 0.003 and 0.1 times the level indicated in Table 1. The level in Table 1 is used to obtain some indication of abnormal requirements, but useful tests in the range of 0.01 to 0.1 times the level of Table 1 are obtained.

Folinic acid. The lowest useful level of folinic acid to detect responses is in the range of 0.03 to 0.1 times the level indicated in Table 1, but in tests in which adenine or serine-glycine interconversion is limiting as much as 10 to 20 times as much folinic acid may be required for an optimal response. Very high levels of folinic acid tend to reduce the response.

Biotin. The level of biotin which is required for a response is substantially below the level indicated in Table 1. In individuals showing a biotin inadequacy, a significant response at levels of 0.01 to 0.03 times that indicated in Table 1 can be obtained but higher levels are needed to detect abnormal requirements. The upper limit would be relatively high.

Vitamin $B_6$. In patients with a deficiency of vitamin $B_6$, useful responses can be obtained at levels of about 0.03 to 0.1 the indicated amount in Table 1, except where glycine and/or serine is omitted under which conditions at least 10 to 20 times as much as indicated in Table 1 for the basal medium have been used. The toxic level would actually be much higher.

Vitamin $B_{12}$. A range of 0.1 to 10,000 $\mu$g/l would be required to test all possible conditions.

Nicotinamide, Thiamine. The toxicities of these have not been determined for an upper limit. In deficient individuals the lower level to show a response would likely be in the range of 0.01 to 0.03 that of Table 1.

Calcium chloride. A decreased response is obtained at 0.1 of the level in Table 1 (i.e., 11.1 mg/l); a near optimal response is obtained at 55.5 mg/l; and for most individuals optimal responses are still obtained at 222 mg/l with some actually requiring this higher amount for an optimal response. At 333 mg/l a decrease in response was obtained with one of four individuals tested. Calcium chloride can be increased about 3 fold of that in Table 1 without significant inhibition of the response in many individual tests. The upper level at which detrimental effects would be a factor are not too much higher.

Magnesium sulfate. Lower limit is about 0.1 of the level in Table 1. Three times the level indicated in Table 1, or 360 mg./l has been used successfully, and up to 5 fold of that in Table 1 results in no significant inhibition of the response.

Ferrous sulfate heptahydrate with ethylenediamine heptahydrate. The lower limit was 0.1 of that indicated in Table 1 in several patients, with one having a good response at 0.05 times that shown in Table 1. Up to three times the level shown in Table 1 has been used successfully, and ten times might be suitable before toxicity would negate the test.

Transferrin can replace the ferrous sulfate, and 0.3 mg/l is the lower limit with slightly reduced response; up to 30 mg/l showed optimal responses. The upper limit for toxicity has not been determined.

Sodium chloride. The concentration of sodium chloride is critical. Even 25% increase or decrease can be significantly detrimental to the test.

Dipotassium hydrogen phosphate. A 4 fold increase decreased the counts from 11,800 to 9,350 which can provide a satisfactory testing result; however, when increased 10 fold of that in Table 1, there was an insufficient response.

Sodium hydroxide. Needed in sufficient amounts to adjust the pH of the medium which can be from pH 6.8 to about 7.6.

Inositol. A concentration of 0.018 mg/l gives about 70% of maximal response, and 0.18 mg/l gives 90–100% of maximal response. 72 mg/l also gives maximal response, thus toxicity would not occur except at very high concentrations. Since inositol is merely stimulatory, omitting it usually causes only a modest decline in response. In one group of individuals, decreased responses up to 50% occurred, but no decrease was observed with the lymphocytes of some individuals.

Choline. A concentration of 0.014 mg/l is inadequate; 0.14 mg/l provides almost a maximal response; and concentrations of 1.4 mg/l to 56 mg provide optimal responses with no significant toxicity for the lymphocytes of most individuals.

Pyruvate. A suitable range is from about 56 mg/l to about 495 mg/l; 16.5 mg/l is inadequate; 1650 mg/l is toxic.

Adenine. 13.5 mg/l is satisfactory, but 135 mg/l shows toxicity. Low limit is approximately 0.1 times the level of Table 1.

PHA. A suitable range is from 1 mg to 20 mg per liter, but the limits vary with the lymphocytes of individual patients.

It is possible to omit one of the vitamins entirely, except pantothenic acid; for example, nicotinamide can be omitted without significantly affecting the response of a large number of patient-isolated lymphocytes.

A single amino acid, such as arginine, or a small group of amino acids, can be increased to high levels without significantly affecting the test for a large proportion of patients. The minimal medium, as set forth in Table 1, has proved most successful in ranges of 0.3 to 3 times the level of amino acids indicated for the basal test medium.

There is a definite minimum requirement for each amino acid for lymphocytes cultured in the minimal medium of Table 1. This limit as well as the upper limit depends on the composition of the medium since the lymphocyte response is frequently the result of a ratio of concentrations rather than a finite concentration of components. This is a result of mutual antagonisms and varies with different patients, as does the minimum requirement.

Enough mitogen should be present to provide maximum stimulation for the number of cells being tested, enough buffer should be present to maintain the pH from about 6.8 to 7.8, enough phenol red should be present to serve as a pH indicator, and sufficient antibiotic should be present to suppress contamination of the culture medium.

The foregoing amounts and ranges provide effective functioning for the respective components of the culture medium.

In the present invention, it is contemplated that the lymphocytes will be incubated in the presence of a medium as described above, in the additional presence of compounds that have side-effects and/or in the further presence of candidate substances that have the potential to ameliorate the side-effects.

b. Separation of Lymphocytes

Lymphocytes may be separated from blood samples in any desired and preferred manner. One of ordinary skill would be aware of a number of standard techniques for retrieving purified lymphocytes from whole blood. The following is provided by example as an exemplary technique as to how the lymphocytes can be separated from blood.

Blood samples are collected in sterile, heparinized, 10 ml. Vacutainer tubes and kept at room temperature for no longer than 30 minutes. Eight ml of sample are layered onto 3 ml of Histopaque (Ficoll and sodium diatrizoate compound obtained from Sigma Chemical Co.) contained in appropriate tubes. Twenty minute centrifugation at 2000 rpm in a NIEC clinical centrifuge separates the erythrocytes from the lymphocytes, the latter remaining in a layer on top of the Histopaque. This layer contains primarly lymphocytes.

The lymphocytes are extracted from the tubes using sterile Pasteur pipettes. Approximately 0.5–2.5 ml of extracted lymphocytes are placed in 15 ml corning plastic centrifuge tubes containing about 6 ml of medium salts, or other appropriate solution. (Generally, two Histopaque tubes are required for 16 ml blood, and the lymphocytes from these tubes are placed in two Corning tubes). The centrifuge tubes are then inverted several times to aid in washing the cells after which they are centrifuged at 1700 rpm for 10 minutes. The supernatant is discarded and the cells in each tube are resuspended in approximately 1 ml of medium salts using gentle aspiration with a sterile Pasteur pipette. The contents of all two tubes are combined into one tube. The tube containing the lymphocytes is inverted several times, then centrifuged at 1700 rpm for 10 minutes and the supernatant is discarded.

The lymphocyte pellet is resuspended in 3 ml of medium salts in the manner just described. The cells are now counted in a Coulter Counter as follows: 20 µl of the suspension is added to 10 ml of Isoton in a plastic Coulter Acuvette and 3 drops of Zapoglobin (Coulter Diagnostics) is added to lyse the erythrocytes so that the lymphocytes can be counted. The solution is gently swirled and counted three times on the Coulter Counter. Based on the average of the three values, the lymphocyte solution is diluted to a concentration of 2.2 million cells per ml with medium salts and recounted. This lymphocyte suspension is then used to inoculate the assay.

The lymphocytes can be isolated from blood according to other methods in the art. For example, the blood obtained from the test person can be rendered non-coagulating in the usual manner, for example, by adding an anti-coagulant such as heparin, and subsequently the lymphocytes are recovered therefrom by known methods, for example, by introducing the blood sample into a column charged with glass beads. Adherent cells adhere to the beads. The lymphocytes can be recovered from the eluate by gradient centrifugation. Alternatively, an adsorption of adherent cells on glass beads may be dispensed with so that gradient centrifugation can be directly employed.

Further suitable processes for obtaining lymphocytes are described, by way of example, in the following references: Johnson and Russel (1965); Boyum (1966); Oppenheimer et al., (1968); Twomey and Sharkey, (1972), all incorporated herein by reference.

All of the lymphocytes, which have been obtained and purified by one of the above methods, may be diluted to an appropriate concentration and this suspension is then used to inoculate the culture medium.

c. Assay

The lymphocyte assay comprises inoculating the culture medium with the test lymphocytes in the presence of a compound, such as for example, a drug with a potential to cause side-effects, and incubating the inoculated culture medium, harvesting the incubated cultures, and comparing the response of lymphocytes exposed to the compound with the response of the lymphocytes exposed to the compound and the substance. In some embodiments, the present invention provides screening methods to identify substances that can overcome the side-effects of the compounds. In such embodiments, the lymphocyte assay is carried out in the additional presence of a substance or candidate substance that has or may have the ability to ameliorate the side effects of the compound.

The following is an example of a lymphocyte assay: Previously sterilized 96 well microtiter plates (Corning) are used in this assay procedure. 0.2 milliliters of the culture medium is added to each well. Where necessary, variable supplements up to 10 µl may be added to each tube, or a smaller volume of an appropriately higher concentration of the medium can be added to the tubes and supplements then added to make a final volume of 0.2 ml. The assay is then inoculated with 10 µl of the diluted lymphocyte suspension (22,000 lymphocytes).

Incubation. The plates are incubated for 4 days at 37° C. in a 5% carbon dioxide atmosphere saturated with water vapor. On the fourth day they are removed and placed in a 37° C. water bath for pulsing with 0.1 $\mu$Ci per tube of $^3$H-thymidine (additionally, tritiated constituents of protein or nucleic acid may be employed) which has a specific activity of 300 $\mu$Ci/mmole. The cultures are then replaced in the incubator for 23–25 hours before harvesting takes place. Other times before harvesting can be used, e.g. 8 hrs., with similar results relative to controls.

Harvesting. The cultures are harvested on a Inotech Biosystems sampling manifold using 0.22 $\mu$m filter papers which are capable of filtering out nucleic acids. The filter papers are positioned on the harvesting plate of the manifold. The media and cells is pulled from the well through the filter. The filter papers are dried for 5 minutes in a drying oven at 120° C. and then counted on a Matrix 96 Beta Counter (Packard).

The above assay procedure can be modified, for example, by carrying out the assay in culture tubes. The same culture medium and the same concentration of supplements (as set forth in Table 1) are used.

The above procedures represent two types of culture conditions, but many other variations are possible in the procedure to achieve the basic concept of assessment of nutritional needs of an individual and to detect differences in requirements based upon biochemical individuality as well as ordinary deficiency states. For example, one may vary the concentrations of some of the medium components. In one specific case, some embodiments of the present invention utilize 5×times the amino acid concentrations described herein with the exception of cysteine and glutamine.

B. Toxicity

The invention contemplates identifying substances that can ameliorate or reverse the toxicity or side effects of a wide variety of compounds. The compounds include drugs, food additives, herbs and herbal extracts, and other chemicals and biochemicals that are used by humans.

a. Statins

Among the clinical drugs the statins are a family of drugs especially targeted by the methods of the present invention. The statin class of drugs are inhibitors of an enzyme, the HMG CoA reductase, which is a liver enzyme involved in cholesterol biosynthesis. Statins are one of the most successful drugs ever developed the first statin being Mevacor (Lovastatin) which was released in 1988. Several randomized double blind clinical trials have consistently demonstrated protection from the development of atherosclerosis as well as tremendous decreases in the clinical events associated with blockages in the vasculature. As heart disease alone is the leading cause of death in the western world the statins provide a significant reduction in mortality and in clinical expenses associate with heart conditions. These mega-trials involving many thousands of people over prolonged time periods have also shown that these drugs are relatively safe. However, a significant population of patients using the statins encounter minor side effects. Like all drugs, certain rare and more serious side effects have also been reported recently.

Some of the reported side effects due to statins include, digestive system effects such as, constipation, diarrhea, upset stomach, gas, heartburn, stomach pain/cramps, anorexia, loss of appetite, nausea, inflammation of the pancreas, hepatitis, jaundice, fatty changes in the liver, and, rarely, severe liver damage and failure, cirrhosis, and liver cancer; muscle and skeletal effects such as, muscle cramps, aches, pain, and weakness; joint pain; muscle breakdown; nervous system effects such as, dizziness, headache, insomnia, tingling, memory loss, damage to nerves causing weakness and/or loss of sensation and/or abnormal sensations, anxiety, depression, tremor, loss of balance, psychic disturbances; skin effects such as, rashes, itching, hair loss, dryness, nodules, discoloration; and visual and sensory effects such as, blurred vision, altered taste sensation, progression of cataracts, eye muscle weakness.

Peripheral neuropathy is one such rare side-effect that has been recently reported with statins and has been reported to occur with any of the 6 currently available statins including, Mevacor, Pravachol, Zocor, Leschol, Lipitor and Baychol. The mechanism is believed to involve reduction of Co Enzyme Q (ubiquinone also called $CoQ_{10}$) and generally stopping the statin therapy results in alleviation of symptoms. Thus, treatment with Co Enzyme Q 10 in large doses also provides recovery of these symptoms. As the biosynthetic pathway of the $CoQ_{10}$ which comprises a polyisoprenoid side chain, is the same as that of cholesterol, starting from acetyl-CoA and proceeding through mevalonate and isopentenylpyrophosphate, $CoQ_{10}$ levels also decrease in patients on therapy with statins (Mortensen et al., 1997; Ghirlanda et al., 1993; Folkers et al., 1990). Exogenous supplementation of $CoQ_{10}$ prevents the plasma reduction induced by the statins (Bargossi et al., 1994).

b. Chemotherapeutic Agents

Drugs used for the treatment of cancers and tumors are generally described as chemotherapeutic agents and include a host of DNA damaging agents such as, methotrexate, doxorubicin, daunorubicin, mitomycin, actinomycin D, bleomycin, plicomycin, taxol, vincristine, vinblastine, cisplatin, VP16, carmustine, melphalan, cyclophosphamide, chlorambucil, busulfan, lomustine, carboplatin, procarbazine, mechlorethamine, camptothecin, ifosfamide, nitrosurea, tamoxifen, raloxifene, estrogen receptor binding agents, gemcitabien, navelbine, farnesyl-protein transferase inhibitors, transplatinum, 5-fluorouracil, temazolomide, and analogs and derivatives of the same. Each chemotherapeutic agent is generally associated with several side effects which include ailments that affect the skin, gasterointestinal tract, the bone marrow, the liver, and the kidney. While some of these ailments and symptoms have effective counteractive measures not all chemotherapeutic agents have substances that can ameliorate side effects. It is contemplated that the methods of the present invention may be used to screen for agents that alleviate the side-effects of the above mentioned and other chemotherapeutic agents.

c. Other Drugs

Several other drugs are also associated with toxicity which in some cases is limited to a few individuals and in other cases is more generally experienced. These are exemplified by the generic categories of, sedatives, anti-inflammatory agents, antibiotics, analgesics, anesthetics, antiviral drugs, etc. For example, antibiotics have side effects ranging from minor gasterointestinal symptoms to more serious effects such as hepatotoxicity, nephrotoxicity, anemia, myalgias, arthralgias, and even cardiotoxicity.

Other non-limiting examples of such drugs include isoniazid which is a drug used for the treatment of tuberculosis and other infections. Common side effects of isoniazid include liver impairment, and peripheral neuropathy which in some cases responds to treatment with pyridoxine. Other occasional side effects include rapid heartbeat and lightheadedness.

Valproic acid, sold under the brand names Depakene, Valproate, or Valrelease, is another class of drugs for which toxicity ameliorating substances are sought. Used to treat seizure related disorders some of the many toxicity symptoms of valproic acid include drowsiness, dizziness, or blurred vision, stomach upset, loss of appetite, headache, or sleep disturbances. More severe symptoms include vomiting, weakness, depression, skin rash, yellowing of the eyes or skin, or severe stomach cramps.

d. Food Additives

In its broadest sense, a food additive is any substance added to food. Food additives are often defined as "any compound the intended use which results or may reasonably be expected to result directly or indirectly in its becoming a component or otherwise affecting the characteristics of any food." This definition includes any compound used in the production, processing, treatment, packaging, transportation or storage of food. In addition, color additives are also added to foods. A color additive is any dye, pigment or substance that can impart color when added or applied to a food. Color additives are also used in drugs, cosmetics, and certain medical devices such as contact lenses.

Such compounds have to be approved by the U.S. Food and Drug Administration (FDA) before they are permitted for human use. However, it is impossible to ascertain the safety of each food additive for each individual. For example, FD&C Yellow No.5, or tartrazine, which is a compound used to color beverages, desert powders, candy ice cream, custards and other foods can cause hives in approximately one out of 10,000 people. Although this is a very small population FD&C Yellow No.5 can causes toxicity to some people. Other examples include the cholesterol substitute olestera, the low-calorie sweetener aspartame, sulfites which are used as preservatives, saccharin, the flavor enhancer monosodium glutamate (MSG) and others. In the case of MSG a very small percentage of the population can develop MSG symptom complex, a condition characterized by one or more of the following symptoms: burning sensation in the back of the neck, forearms and chest numbness in the back of the neck, radiating to the arms and back tingling, warmth and weakness in the face, temples, upper back, neck and arms facial pressure or tightness chest pain headache nausea rapid heartbeat bronchospasm (difficulty breathing) in MSG-intolerant people with asthma drowsiness weakness. Thus, substances that can reverse the side effects of these commonly used food additives and food colors are actively sought.

e. Components of Social Drugs

Social drugs such as alcoholic beverages, carbonated beverages, coffee, kolas, and teas comprise components that can have toxicity especially when consumed in high doses or even if consumed chronically. These components include ethanol, caffeine, theophylline, theobromine and other methyl xanthines. All these agents are known to affect the central nervous system (CNS). For example, caffeine, a component of coffee, tea, chocolate, colas, as well as several across the counter drugs, is a CNS stimulant. Caffeine also stimulates the cardiovascular system, raising blood pressure and heart rate. Methylxanthines in general, which includes caffeine, theophylline and theobromine, also increase the respiratory rate and act as bronchodialators. Ethanol on the other hand is a CNS depressant. Ethanol in high doses and consumed chronically also causes liver toxicity. Yet other side effects of higher doses of ethanol and/or caffeine intake by pregnant women include birth defects.

e. Herbs

Herbs and herbal extracts are widely used as alternative therapies by a significant percentage of the population. However, these remedies are also often associated with side effects. For example, the popular herb ginseng can cause toxicites such as headaches, insomnia, anxiety, breast soreness or tenderness, skin rashes, asthma attacks, increased blood pressure, diarrhea, euphoria, nervousness, skin eruptions, heart palpitations, or post-menopausal uterine bleeding. Others such as ginkgo biloba can cause spontaneous bleeding; St. John's wort can cause gastrointestinal disturbances, allergic reactions, fatigue, dizziness, confusion, photosensitivity; the herb ephedra can cause hypertension, insomnia, arrhythmia, nervousness, tremor, headache, seizure, cerebrovascular event, myocardial infarction, and kidney stones; and kava can cause sedation, oral and lingual dyskinesia, exacerbation of Parkinson's disease, painful twisting movements of the trunk, and rashes. As herbal supplements and therapies are rapidly gaining popularity agents that can ameliorate herbal side effects are widely sought in the art.

C. Screening Methods

The present invention comprises methods for identifying substances that can overcome the toxic-effects of compounds. These methods may comprise random screening of large libraries of candidate substances. Alternatively, the methods may be used to focus on particular classes of substances selected with an eye towards structural attributes that are believed to make them more likely to modulate the function of the compound that can cause the toxicity.

To identify a substance that can ameliorate toxicity of a compound, one generally will determine the ability of the substance with respect to ameliorating the toxicity in the presence and absence of the compound. For example, a method generally comprises:

(a) providing a candidate substance;

(b) administering the candidate substance to a cell, or a suitable experimental animal in the presence of a compound that causes toxicity in the cell or experimental animal;

(c) measuring one or more characteristics of the cell or animal in step (b); and (d) comparing the characteristic measured in step (c) with the characteristic of the cell or animal in the absence of the candidate substance, wherein a difference between the measured characteristics indicates that the candidate substance is, indeed, a substance that can ameliorate the toxicity of the compound in the cell or animal.

The screening and/or identification assays may be conducted in cell free systems, in isolated cells, or in organisms including transgenic animals. In the present invention a preferred embodiment is performing the assay in isolated and cultured lymphocyte cells.

As used herein the term "candidate substance" refers to any molecule that may potentially ameliorate, inhibit, reduce, decrease or reverse the toxicity or side effects caused by a compound. A candidate substance may be derived from a variety of sources. One may simply acquire, from various commercial sources, small molecule libraries that are believed to meet the basic criteria for useful drugs in an effort to "brute force" the identification of useful substances. Screening of such libraries, including combinatorially generated libraries (e.g., peptide libraries, chemical libraries, oligonucleotide libraries), is a rapid and efficient way to screen large number of related (and unrelated) substances for activity. Combinatorial approaches also lend themselves to rapid evolution of potential drugs by the creation of second, third and fourth generation substances modeled of active, but otherwise undesirable substances.

Candidate substances may include fragments or parts of naturally-occurring substances, or may be found as active combinations of known substances, which are otherwise inactive. It is proposed that substances isolated from natural sources, such as animals, bacteria, fungi, plant sources, including leaves and bark, and marine samples may be assayed as candidates for the presence of potentially useful pharmaceutical agents that can reverse the toxic-effects of compounds. It will be understood that the substances to be screened could also be derived or synthesized from chemical compositions or man-made substances. Thus, it is understood that the candidate substance identified by the present invention may be a chemical compound or a biochemical compound. Examples include, proteins, peptides, amino-acids, small molecules, nucleic acids, lipids, nutritional supplements such as vitamins or minerals, drugs, or any other substance that may be designed through rational drug design starting from known inhibitors or stimulators of biological components involved in toxicity pathways.

Other suitable substances include antisense molecules, ribozymes, and antibodies (including single chain antibodies), each of which would be specific for the target molecule that the compound causing toxicity affects. For example, an antisense molecule that bound to a translational or transcriptional start site, or splice junctions, of a particular nucleic acid that is involved in the toxicity of the compound would be one example of an ideal candidate inhibitor.

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

D. Characterization and Isolation of the Plasma Composition

The present invention also provides a composition comprised in the plasma that has the ability to ameliorate the toxicity of metabolic inhibitors such as the statins. Heating plasma samples, which comprise the plasma derived composition of the invention, to 80° C. renders the plasma composition inactive with respect to its ability to ameliorate the toxicity of the metabolic inhibitors. Filtration of the plasma sample using an Amicon Microcon filter device indicates that the plasma composition has a molecular weight of at least 100,000. It is contemplated that the plasma composition may comprise at least one peptide, a polypeptide, a protein or a small molecule which is associated with or bound to at least one peptide, polypeptide, or protein. The plasma composition may also comprise a lipid moiety, and/or a carbohydrate moiety and/or a nucleic acid component. As the plasma composition is heat-labile, it is contemplated to comprise at least one heat-labile peptide, polypeptide, or protein that may additionally be associated with or bound to at least one small molecule which may be a lipid moiety, and/or a carbohydrate moiety and/or a nucleic acid moiety.

Thus, in certain embodiments, the present invention concerns a novel composition comprising at least one proteinaceous molecule. As used herein, a "proteinaceous molecule," "proteinaceous composition," "proteinaceous compound," or "proteinaceous material" generally refers, but is not limited to, a protein of greater than about 200 amino acids or the full length endogenous sequence translated from a gene; a polypeptide of greater than about 100 amino acids; and/or a peptide of from about 3 to about 100 amino acids. All the "proteinaceous" terms described above may be used interchangeably herein.

In certain embodiments the size of the at least one proteinaceous molecule may comprise, but is not limited to, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 275, about 300, about 325, about 350, about 375, about 400, about 425, about 450, about 475, about 500, about 525, about 550, about 575, about 600, about 625, about 650, about 675, about 700, about 725, about 750, about 775, about 800, about 825, about 850, about 875, about 900, about 904, about 925, about 950, about 975, about 1000, about 1100, about 1200, about 1300, about 1400, about 1500, about 1750, about 2000, about 2250, about 2500, about 3000, about 4000, about 4014, about 5000, about 10,000 or greater amino molecule residues, and any range derivable therein.

As used herein, an "amino molecule" refers to any amino acid, amino acid derivative or amino acid mimic as would be known to one of ordinary skill in the art. In certain embodiments, the residues of the proteinaceous molecule are sequential, without any non-amino molecule interrupting the sequence of amino molecule residues. In other embodiments, the sequence may comprise one or more non-amino molecule moieties. In particular embodiments, the sequence of residues of the proteinaceous molecule may be interrupted by one or more non-amino molecule moieties.

Accordingly, the term "proteinaceous composition" encompasses amino molecule sequences comprising at least one of the 20 common amino acids in naturally synthesized proteins, or at least one modified or unusual amino acid, including but not limited to those shown on Table 2 below.

TABLE 2

Modified and Unusual Amino Acids

| Abbr. | Amino Acid | Abbr. | Amino Acid |
|---|---|---|---|
| Aad | 2-Aminoadipic acid | EtAsn | N-Ethylasparagine |
| Baad | 3-Aminoadipic acid | Hyl | Hydroxylysine |
| Bala | β-alanine, β-Amino-propionic acid | AHyl | allo-Hydroxylysine |
| Abu | 2-Aminobutyric acid | 3Hyp | 3-Hydroxyproline |
| 4Abu | 4-Aminobutyric acid, piperidinic acid | 4Hyp | 4-Hydroxyproline |
| Acp | 6-Aminocaproic acid | Ide | Isodesmosine |
| Ahe | 2-Aminoheptanoic acid | AIle | allo-Isoleucine |
| Aib | 2-Aminoisobutyric acid | MeGly | N-Methylglycine, sarcosine |
| Baib | 3-Aminoisobutyric acid | MeIle | N-Methylisoleucine |
| Apm | 2-Aminopimelic acid | MeLys | 6-N-Methyllysine |
| Dbu | 2,4-Diaminobutyric acid | MeVal | N-Methylvaline |
| Des | Desmosine | Nva | Norvaline |
| Dpm | 2,2'-Diaminopimelic acid | Nle | Norleucine |
| Dpr | 2,3-Diaminopropionic acid | Orn | Ornithine |
| EtGly | N-Ethylglycine | | |

In further embodiments the proteinaceous composition comprises a biocompatible protein, polypeptide or peptide.

As used herein, the term "biocompatible" refers to a substance which produces no significant untoward effects when applied to, or administered to, a given organism according to the methods described herein. Organisms include, but are not limited to, mammals such as humans, horses, dogs, cows, sheep, pigs and the like. Such untoward or undesirable effects are those such as significant toxicity or adverse immunological reactions. In preferred embodiments, biocompatible protein, polypeptide or peptide containing compositions will generally be mammalian proteins or peptides or synthetic proteins or peptides each essentially free from toxins, pathogens and harmful immunogens.

a. Purification of the Plasma Composition

As the plasma composition of the invention has therapeutic benefits in terms of ameliorating the toxic effect of the statins, it will be desirable to purify the plasma composition. Methods for purifying plasma are well known in the art. In some embodiments, it is contemplated that the plasma composition may further be identified by purification methods such as those described below:

(i) Purification of the Protein Component(s) of the Composition from Plasma

Plasma will be isolated from a mammalian animal using methods known to the skilled artisan and subject to protein purification. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of the protein or polypeptide or peptide comprising the plasma composition of the invention. The term "purified protein or polypeptide or peptide" as used herein, is intended to refer to a composition, isolatable from other components, wherein the protein or polypeptide or polypeptide or peptide is purified to any degree relative to its naturally-obtainable state. A purified protein or polypeptide or peptide therefore also refers to a protein or polypeptide or peptide, free from the environment in which it may naturally occur.

Generally, "purified" will refer to a composition comprising a protein or polypeptide or peptide that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition. The term "isolated", when used to describe the composition disclosed herein, means protein that has been identified and separated and/or recovered from a component of its natural environment. Contaminant components of its natural environment are materials that would interfere with preventive or therapeutic uses for the protein, and may include other proteinaceous or non-proteinaceous solutes. In one embodiments, the protein may be purified (1) to a degree sufficient to obtain at least 15 residues of N-terminal or internal amino acid sequence, or (2) to homogeneity by SDS-PAGE under non-reducing or reducing conditions using Coomassie blue or, preferably, silver stain. "Essentially pure" protein means a composition comprising at least about 90% by weight of the protein, based on total weight of the composition, preferably at least about 95% by weight. "Essentially homogeneous" protein means a composition comprising at least about 99% by weight of protein, based on total weight of the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "fold purification number." The actual units used to represent the amount of activity will, of course, be dependent upon the particular assay technique chosen to follow the purification and whether or not the protein or peptide exhibits a detectable activity. In the instant invention the plasma composition comprising at least one heat-labile peptide, polypeptide, protein or a small molecule associated with at least one heat-labile peptide, polypeptide, or protein, having a molecular weight of at least 100,000, can be detected by its activity that ameliorates the toxicity of statins in a lymphocyte-culture assay. Such an assay is described further in 'Example 1' later in the specification.

Various techniques suitable for use in protein purification will be well known to those of skill in the art. These include, for example, precipitation with ammonium sulphate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide comprising the plasma composition always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1977). It will therefore be appreciated that under differing electrophoresis conditions, the apparent molecular weights of purified or partially purified expression products may vary.

High Performance Liquid Chromatography (HPLC) and FPLC are characterized by a very rapid separation with extraordinary resolution of peaks. This is achieved by the use of very fine particles and high pressure to maintain an adequate flow rate. Separation can be accomplished in a matter of minutes or at most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and Helix pomatia lectin. Lectins themselves are purified using affinity chromatography with carbohydrate ligands. Lactose has been used to purify lectins from castor bean and peanuts; maltose has been useful in extracting lectins from lentils and jack bean; N-acetyl-D galactosamine is used for purifying lectins from soybean; N-acetyl glucosaminyl binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography.

It is contemplated that the proteinaceous composition of the invention may be made by any technique known to those of skill in the art, including the expression of proteins, polypeptides or peptides through standard molecular biological techniques, the isolation of the proteinaceous compound from natural sources, or the chemical synthesis of proteinaceous materials. The nucleotide and protein, polypeptide and peptide sequences for various genes have been previously disclosed, and may be found at computerized databases known to those of ordinary skill in the art. One such database is the National Center for Biotechnology Information's Genbank and GenPept databases (http://www.ncbi.nlm.nih.gov/). The coding regions for these known genes may be amplified and/or expressed using the techniques know to those of ordinary skill in the art. Alternatively, various commercial preparations of proteins, polypeptides and peptides are known to those of skill in the art.

F. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Reversal of Statin Toxicity

Statins are used to reverse cholesterol toxicity. All of the compounds used to inhibit cholesterol biosynthesis were found to be inhibitory to the growth or other response of lymphocytes at 0.1 $\mu$g/ml. This inhibitory effect can be reversed in some cases by the administration of Co enzyme $Q_{10}$ (Co$Q_{10}$) or a combination of Co$Q_{10}$ and plasma. Most of the studies were performed using Lipitor. In addition to cholesterol inhibitors, other drugs and food/drug additives with potential toxic-effects have been analyzed.

The medium used in this study was the same as described previously (See U.S. Pat. No. 4,499,064, herein expressly incorporated by reference) except that the concentration the amino acids used was increased five fold. The medium is also described in the specification above. Various concentrations of amino acids can be used in the medium to determine the effect on growth or growth inhibition.

Human peripheral blood was collected from a group of patients in the clinic. Lymphocytes were isolated as described (Shive, 1986), counted in a Coulter Counter, and inoculated into the medium at a concentration of 110,000 cells per ml. Experiments were conducted in 96 well microtite plates. Triplicate samples were run in all experiments. Lipitor was added at the indicated concentrations. For reversal of toxicity Co$Q_{10}$ was added at a concentration of 0.5 $\mu$g/ml, and the patient's own plasma at a concentration of 0.1%. All chemicals were obtained from Sigma Chemical Corporation. The samples were incubated for four days in a Forma Incubator at 37.5° C. in a 5% $CO_2$ high humidity atmosphere. Cells were then pulsed with 10 $\mu$l [$^3$H]-thymidine (0.29×10–6M final concentration; specific activity 1 Ci/mol). Twenty-four hours later, cells were harvested using an Inotech Cell Harvester. Radioactive incorporation was measured using a Packard Matrix 96 Beta Counter. As a preliminary study, lymphocytes were tested under these conditions.

Figure 1:
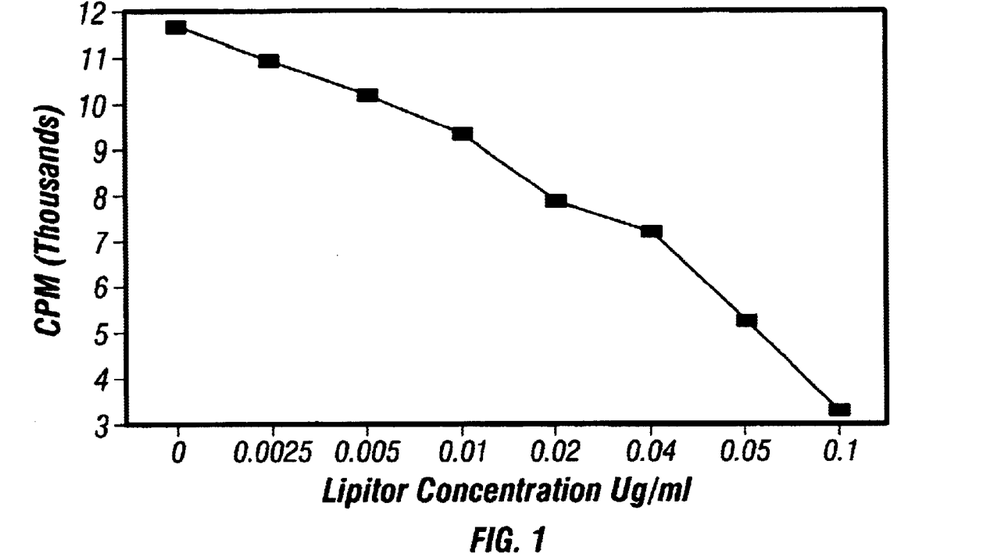
FIG. 1. Lipitor toxicity.

As shown in FIG. 1, Lipitor was extremely toxic to most subjects at a concentration of 0.1 µg/ml. Since the patients take between 10 and 80 milligrams/day, this observation was alarming. Obviously, the drug is not this toxic in vivo. Addition of 0.1% plasma to the test reversed the toxic-effect for some, but not all, subjects. The statin is an effective inhibitor of cholesterol biosynthesis. Since cholesterol and $CoQ_{10}$ share the same biosynthetic pathway, $CoQ_{10}$ was tested for reversing effects. It offers some protection, but it is not totally effective alone. A combination of plasma and $CoQ_{10}$ was the most effective in reversing toxicity.

Investigation of the factor present in the plasma demonstrated that it is a large molecule or molecules with a molecular weight greater than 100,000 and that it is heat labile. It appears that this molecule may function as a carrier or transport protein for an additional cofactor or cofactors. This test can be used to determine deficiencies of $CoQ_{10}$ and also deficiencies related to the expression or function of this large molecule in the patient's plasma.

Figure 2:
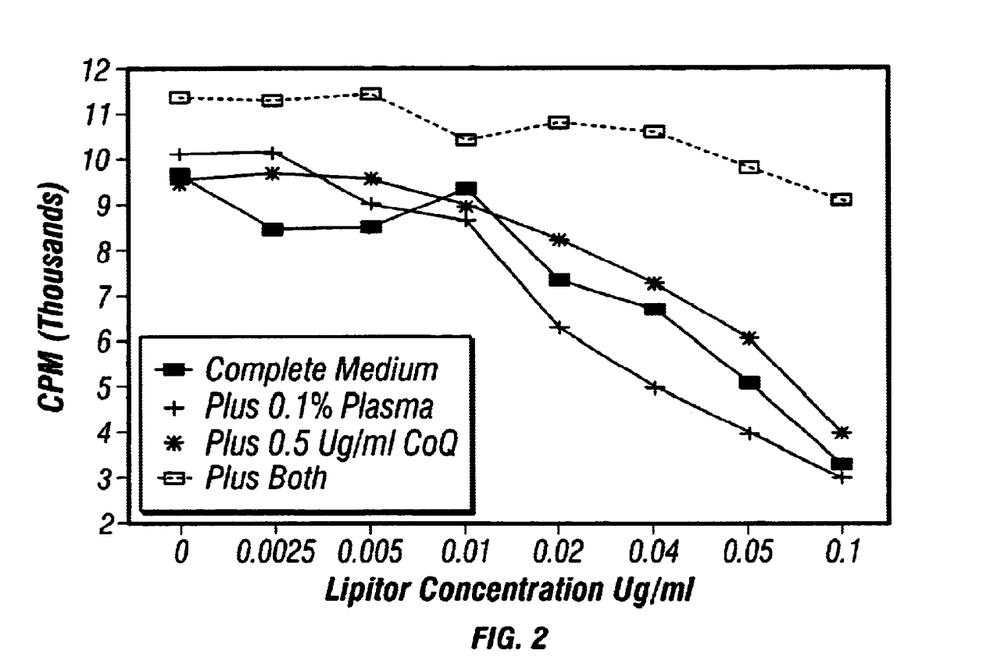
FIG. 2. Reversal of lipitor toxicity in the presence and absence of plasma, or CoQ, or both in a patient.

Patients fell into three categories. Many of them required both plasma and $CoQ_{10}$ to reverse toxicity (FIG. 2). These individuals should probably take $CoQ_{10}$ along with the medication. These patients appear to have the plasma factor present in their plasma.

Figure 3:
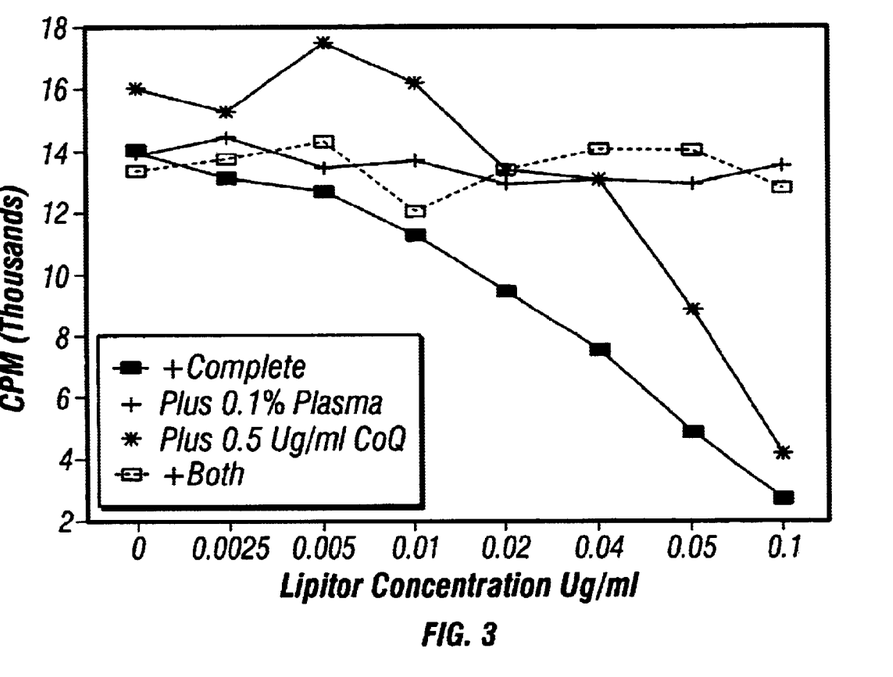
FIG. 3. Reversal of lipitor toxicity in the presence and absence of plasma, or CoQ, or both in a patient.

A second group (FIG. 3) was reversed by plasma alone. Apparently, the $CoQ_{10}$ concentration of their plasma is high enough to effect reversal. This group can take the medication, but should monitor the $CoQ_{10}$ level in their plasma since $CoQ_{10}$ synthesis is being inhibited.

Figure 4:
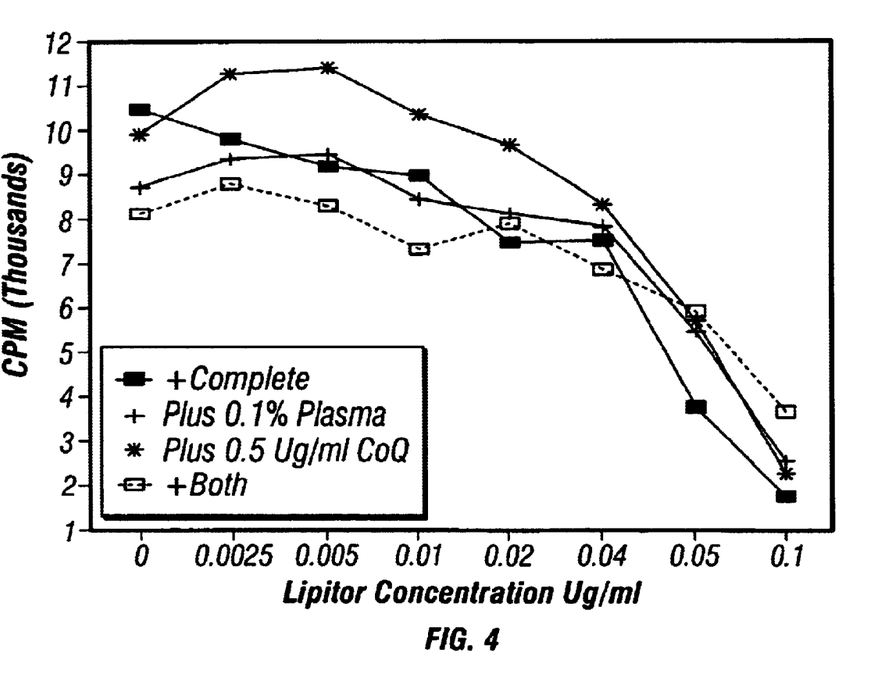
FIG. 4. Lipitor toxicity in the presence and absence of plasma, or CoQ, or both in a patient.

A third group (FIG. 4) was inhibited by Lipitor even in the presence of both CoQ and their plasma. Apparently, this population is lacking at least two factors and would be subject to possible side effects from taking the drug.

This procedure could be used to evaluate all drugs before they are prescribed for individuals. This could be a valuable first step in approving a particular substance for use in human trials. This technique has been used to study the toxicity of many other commonly used additives and drugs shown in Table 3. Studies can be conducted to assess the toxicity of various compounds encountered by the general public in proscribed drugs, over the counter medications, herbs, and herbal extracts.

TABLE 3

| Additive Tested | Amount Required to Inhibit Growth by 50% |
|---|---|
| Lipitor | <0.0001 mg/ml |
| Pravachol | <0.0001 mg/ml |
| Zocor | <0.0001 mg/ml |
| Mevacor | <0.0001 mg/ml |
| Diazepam | 0.02 mg/ml |
| Aluminum | 0.005 mg/ml |
| Theophyline | 0.03 mg/ml |
| Monosodium Glutamate | 7.5 mg/ml |
| Caffeine | 0.0776 mg/ml |
| Isoniazid | 0.548 mg/ml |
| Retanol | 0.0005 mg/ml |
| Methothrexate | <0.00002 mg/ml |
| Ethanol | 10.0 mg/ml |
| Salicylate | 0.005 mg/ml |
| Acetyl Salicylate | 0.005 mg/ml |
| Valproic Acid (Depakote) | 0.4 to 1.2 µg/ml |

Some compounds that were tested but did not show toxicity in lymphocytes are phenobarbitol at concentrations of up to 0.02 mg/ml, neuronton at concentrations of up to 0.2 mg/ml, triazolam at concentrations of up to 0.02 mg/ml, glucoseamine at concentrations of up to 0.2 mg/ml.

All of the METHODS and COMPOSITIONS disclosed and claimed herein can be made and executed without undue experimentation in light of the present disclosure. While the compositions and methods of this invention have been described in terms of preferred embodiments, it will be apparent to those of skill in the art that variations may be applied to the METHODS and COMPOSITIONS and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Bargossi A M, Battino M, Gaddi A, Fiorella P L, Grossi G, Barozzi G, Di Giulio R, Descovich G, Sassi S, Genova M L, "Exogenous CoQ10 preserves plasma ubiquinone levels in patients treated with 3-hydroxy-3-methylglutaryl coenzyme A reductase inhibitors," *Int J Clin Lab Res.*, 24(3):171–6, 1994.

Boyum, A., Scand. *J. Clin. Lab. Invest. Suppl.* 77, 1966.

Folkers K, Langsjoen P, Willis R, Richardson P, Xia L J, Ye C Q, Tamagawa H, "Lovastatin decreases coenzyme Q levels in humans," *Proc Natl Acad Sci USA,* November;87(22):8931–4, 1990.

Ghirlanda G, Oradei A, Manto A, Lippa S, Uccioli L, Caputo S, Greco A V, Littarru G P, "Evidence of plasma CoQ10-lowering effect by HMG-CoA reductase inhibitors: a double-blind, placebo-controlled study," *J Clin Pharmacol, March;*33(3):226–9, 1993.

Johnson, G. J. and Russel, P. S., *Nature,* 208, pp. 343, 1965.

Mortensen S A, Leth A, Agner E, Rohde M, "Dose-related decrease of serum coenzyme Q10 during treatment with HMG-CoA reductase inhibitors," *Mol Aspects Med,* 18 Suppl:S137–44 1997.

Oppenheimer, J. J., Leventhal, P. G., Hersh, E. M., *Journal Immunology,* 101, pp. 262–270, 1968.

Shive, W. (1984) Development of lymphocyte culture methods for assessment of the Nutritional and metabolic status of individuals. *J. Int. Acad. Prev. Med.,* 8, 5–16.

Shive, W., Pinkerton, F., Humphreys, J., Johnson, M., Hamilton, W. G., and Matthews, K. S. (1986) Development of a chemically defined serum- and Protein-free medium for growth of human peripheral lymphocytes. *Proc Natl Acad Sci U.S.A.,* 83, 9–13.

Twomey, J. J., Sharkey, O., *Journal of Immunology,* 108, pp. 984–990, 1972.

U.S. Pat. No. 4,499,064

What is claimed is:

1. A method for testing a substance for the ability of the substance to ameliorate the toxic-effects of a compound, comprising the steps of:
   a) incubating lymphocytes in the presence of the compound and in the presence and absence of the substance; and
   b) comparing the toxic-effect of the compound on the lymphocytes incubated in the presence of the substance to the effect of the compound on the lymphocytes in the absence of the substance, wherein the toxic-effect of the compound is assessed by assessing its effect on the amount of ATP synthesized by the lymphocytes.

2. The method of claim 1, wherein the amount of ATP synthesized is measured by fluorimetric methods.

3. The method of claim 1, further comprising determining the lowest dosage at which a substance can ameliorate the toxic effect of said compound.

4. The method of claim 1, wherein the compound is a clinical drug, a teratogenic agent, a social drug, a drug additive, a food additive, a food component, an herb, an herbal extract, or a chemical compound.

5. The method of claim 1, wherein the compound is comprised in a plant or a mushroom.

6. The method of claim 4, wherein the clinical drug is a metabolic inhibitor.

7. The method of claim 6, wherein said metabolic inhibitor is a stalin.

8. The method of claim 7, wherein said statin is lip itor, mevacor, pravachol, zocor, Baychol, Cerivastatin, or Fluvastatin.

9. The method of claim 4, wherein the clinical drug is a sedative.

10. The method of claim 9, wherein the sedative is diazepam.

11. The method of claim 4, where the clinical drug is a chemotherapeutic agent.

12. The method of claim 11, wherein the chemotherapeutic agent is methotrexate, 5-fluorouracil, doxorubicin, daunorubicin, mitomycin, actinomycin D, bleomycin, plicomycin, taxol, vincristine, vinbiastine, cisplatin, VP16, carmustine, meiphalan, cyclophosphamide, chlorambucil, busulfan, lomustine, carboplatin, procarbazine, mechiorethamine, camptothecin, ifosfamide, nitrosurea, tamoxifen, raloxifene, estrogen receptor binding agents, gemcitabien, navelbine, farnesyl-protein transferase inhibitors, transpiatinum or temazolomide.

13. The method of claim 4, wherein the clinical drug is an anti-inflammatory agent.

14. The method of claim 13, wherein the anti-inflammatory agent comprises salicylate and/or acetyl salicylate.

15. The method of claim 14, where the anti-inflammatory agent is ibuprofen, ketoprofen, piroxicam, naproxen, naproxen sodium, sulindac, aspirin, choline subsalicylate, diflunisal, oxaprozin, diclofenac sodium delayed release, diclofenac potassium immediate release, etodolac, ketorolac, fenoprofen, flurbiprofen, indomethacin, fenamates, meclofenamate, mefenamic acid, nabumetone, oxicam, piroxicam, salsalate, tolmetin, or magnesium salicylate.

16. The method of claim 13, wherein the anti-inflammatory agent comprises a steroid.

17. The method of claim 16, wherein the steroid is dexamethason, hydrocortisone, methylprednisolone, prednisone, or triamcinolone.

18. The method of claim 4, wherein the clinical drug is isoniazid.

19. The method of clain 4, wherein the clinical drug is valproic acid.

20. The method of claim 4, wherein the clinical drug is retinol.

21. The method of claim 4, wherein the teratogenic agent is thalidomide.

22. The method of claim 4, wherein the food additive is monosodium glutamate, aspartame or saccharin.

23. The method of claim 4, wherein the chemical compound comprises a metal.

24. The method of claim 23, wherein the metal is aluminum.

25. The method of claim 23, wherein the metal is copper.

26. The method of claim 4, wherein the social drug comprises ethanol, theophylline, caffeine or theobromine.

27. The method of claim 1, wherein the substance is a nutritional supplement, a protein, a peptide, an amino acid, a chemical, a biochemical, a small molecule, or a pharmaceutical agent.

28. The method of claim 1, wherein the substance is LDL.

29. The method of claim 1, further comprising a control comprising:
   a) incubating the lymphocytes with a compound with a known toxicity in the presence of a substance known to reverse said known toxicity; and
   b) analyzing the effect on lymphocytes.

30. A method for ameliorating toxicity in a patient undergoing therapy with a compound that has a known toxicity comprising, administrating to said patient a substance identified in accordance with the method of claim 1.

31. The method of claim 30, wherein said patient is human patient.

32. A method for ameliorating toxicity in a patient undergoing therapy with a compound that has a known toxicity comprising:
   a) isolating lymphocytes from said patient;
   b) incubating lymphocytes in the presence of the compound and in the presence and absence of a candidate substance that can reverse the toxicity of said compound;
   c) comparing the toxic-effect of the compound on the lymphocytes incubated in the presence of the candidate substance to the effect of the compound on the lymphocytes in the absence of the candidate substance thereby identifying a substance that can reverse toxicity. wherein the toxic-effect of the compound is assessed by assessing its effect on the amount of ATP synthesized by the lymphocytes; and
   d) administrating to said patient the identified substance that can reverse toxicity of the compound.

33. The method of claim 32, wherein said patient is human patient.

34. A composition comprising one or more factors characterized by the following properties:
   a) isolatable from mammalian plasma;
   b) containing at least one heat-labile component having a molecular weight of at least 100,000; and
   c) having the ability to ameliorate the toxicity of a metabolic inhibitor.

35. The composition of claim 34, wherein the mammalian plasma is human plasma.

36. The composition of claim 34, wherein said metabolic inhibitor is a statin.

37. The composition of claim 36, wherein said statin is lipitor, mevacor, pravachol, zocor, Baychol, Cerivastatin, or Fluvastatin.

38. The method of claim 1, wherein said lymphocytes are further incubated in a chemically defined medium.

39. The method of claim 1, wherein the toxic-effect of the compound is assessed by assessing the effect of said compound on the growth of the lymphocytes.

40. The method of claim 1, wherein the toxic-effect of the compound is assessed by assessing the effect of said compound on the cell-size of the lymphocytes.

41. The method of claim 1, wherein the toxic-effect of the compound is assessed by assessing the effect of said compound on the morphology of the lymphocytes.

* * * * *

UNITED STATES PATENT AND TRADEMARK OFFICE
CERTIFICATE OF CORRECTION

PATENT NO.    : 6,723,527 B2
DATED         : April 20, 2004
INVENTOR(S)   : Pettit et al.

It is certified that error appears in the above-identified patent and that said Letters Patent is hereby corrected as shown below:

Column 27,
Line 15, delete "stalin" and insert -- statin -- therefor.
Line 16, delete "lip itor" and insert -- lipitor -- therefor.
Line 28, delete "vinbiastine" and insert therefor -- vinblastine -- therefor.
Line 29, delete "meiphalan" and insert -- melphalan -- therefor.
Line 31, delete "mechiorethamine" and insert -- mechlorethamine -- therefor.
Line 34, delete "transpiatinum" and insert -- transplatinum -- therefor.

Column 28,
Line 34, delete "ity. wherein" and insert -- ity, wherein -- therefor.

Signed and Sealed this

Thirtieth Day of November, 2004

JON W. DUDAS
*Director of the United States Patent and Trademark Office*